United States Patent [19]

Rongone et al.

[11] 4,095,465

[45] Jun. 20, 1978

[54] TESTING ADHESION OF CORD OR WIRE IN RUBBER

[75] Inventors: Ronald L. Rongone, Cuyahoga Falls; David W. Nicholson, Kent; Roger E. Payne, Akron, all of Ohio

[73] Assignee: The Goodyear Tire & Rubber Company, Akron, Ohio

[21] Appl. No.: 781,245

[22] Filed: Mar. 25, 1977

[51] Int. Cl.$^2$ .............................................. G01L 5/04
[52] U.S. Cl. ...................................... 73/159; 264/271
[58] Field of Search ................... 73/150, 159, 96, 146; 264/259, 271, 275, 299

[56] References Cited

U.S. PATENT DOCUMENTS

| | | | |
|---|---|---|---|
| 2,665,582 | 1/1954 | Armstrong et al. | 73/159 |
| 4,041,806 | 8/1977 | Klar | 73/159 |

*Primary Examiner*—Richard C. Queisser
*Assistant Examiner*—Joseph W. Roskos
*Attorney, Agent, or Firm*—R. S. Washburn

[57] ABSTRACT

A novel method and mold apparatus for testing adhesion of cord or wire in rubber which measures "intrinsic" adhesion, i.e. adhesive strength independently of the tearing strength and stiffness of the rubber matrix. Each test specimen is formed of two uncured preformed or premolded blocks, called coupons, in respective preform molds. Two wire segments are inserted coaxially between the coupons in preformed grooves and the assembly is molded and cured. The proximate ends of the segments are buried in or embedded within the body of the specimen, but spaced apart along the axis of the wire segments and the body of the test specimen. The specimen is stressed only by the wire segments. In an Instron or like test machine, the free ends of the wire segments are pulled at a selected rate to failure. Failure of the adhesion is observed to start at the embedded end of the wire segment and progress outwardly along the segment which is pulled from the body or matrix. The force required is recorded and the maximum observed force, together with the otherwise determined rubber stiffness, provides a measure of the intrinsic face-to-face adhesion of the particular wire to the particular rubber. A preferred mold apparatus provides mold plates useful both in preforming the coupons and in mold curing the specimens.

10 Claims, 7 Drawing Figures

TESTING ADHESION OF CORD OR WIRE IN RUBBER

The present invention relates to testing the interface adhesion of filar reinforcement elements and elastomeric compounds and particularly to such testing of wire to rubber. More particularly the invention provides a method for preparing and testing a specimen including a body of the rubber compound, the body having a pair of linearly aligned wire segments embedded therein with the proximate ends of the wire segments spaced a predetermined minimum distance apart. The invention also provides specimen forming and molding apparatus for the practice of the method in accordance with the invention.

BACKGROUND OF THE INVENTION

The standard method of test for adhesion of vulcanized rubber to wire in use at the present time is set forth in ASTM standard designation D1871-68 with modifications according to ASTM D2229-73. This test is referred to herein as the Standard Block Adhesion Test or SBAT. These standard tests now in use have long been known not to be fully satisfactory, one objection being the wide scatter of measured results obtained in tests of seemingly identical samples, and a second objection being their inability to distinguish the effect of intrinsic adhesion from the effects of rubber stiffness and rubber tearing strength. We have discovered that some of the disadvantages are related to the fact that the wire or wires extend continuously through the body of the sample and that difficulties experienced are also associated with the fact that the elastomeric body of the sample must be restrained or confined to resist the pull exerted on the wire of the specimen.

We have also discovered by the use of photoelastic techniques that to overcome the objections and disadvantages of the prior testing for adhesion that the end of the wire of the specimen must be embedded within the body of the specimen as distinguished from extending through the body. We have further discovered that the body is advantageously subjected only to the pull of the wire and not to any external restraint and, further, that this can be accomplished conveniently by embedding two collinear wire segments the proximate ends of which are spaced apart not less than a predetermined minimum distance within the body of the specimen.

It is, therefore, the object of the invention to provide a method and apparatus for testing the intrinsic interface adhesion between wire and rubber improved with respect to the methods and apparatus heretofore in use.

Broadly, the invention provides a method of testing interface adhesion of wire and rubber comprising:

preparing two wire segments each of predetermined length;

preforming two coupons of uncured rubber to provide for a fresh, uncontaminated face and a predetermined volume;

placing said wire segments, each with a length portion thereof in seated contact with said fresh face of one of said preformed coupons and the remaining length portions thereof extending freely outward lengthwise of such coupon along a single straight line and with the proximate ends of the segments spaced apart along said line, then placing said fresh face of the other of said coupons in face to face contact with the fresh face of said one thereof and thereby embedding the first said length of each said segment and forming a unitary body of the pair of coupons with the proximate ends of two wire segments embedded in and spaced apart in such body a predetermined minimum distance;

pulling said wire segments apart at a predetermined rate while maintaining said body free of restraint;

measuring the force required in said pulling, the force so measured being useful to determine, together with otherwise known rubber stiffness, interface adhesion of said wire and rubber.

Further, the invention provides a specimen molding apparatus for the wire to rubber adhesion test comprising means for preforming a pair of coupons of uncured rubber each having a fresh uncontaminated uncured surface and predetermined volume;

means for seating a pair of wire segments in straight line spaced apart array in one of said fresh surfaces;

mold means for matingly juxtaposing said surfaces with said wire segments there between to form the uncured specimen;

means for compressing said uncured specimen while curing the same; and vent means for controlling flow of said rubber in and from said specimen during said curing.

To acquaint persons skilled in the arts most closely related to the present invention, certain preferred embodiments thereof illustrating a best mode now contemplated for putting the invention into practice are described herein by and with reference to the annexed drawings forming a part of the specification. The embodiments shown and described herein are illustrative and as will become apparent to those skilled in these arts can be modified in numerous ways within the spirit and scope of the invention defined in the claims hereof.

The term "rubber" is used throughout the specification and claims to simplify the description and language. The term "rubber" will be understood in a broad generic sense to include natural rubber, synthetic rubbers, combinations and compositions of natural and synthetic rubbers, and elastomeric compounds and compositions commonly used in engineered products such as tires, belts, hose, and the like, wherein adhesion between rubber and wire is of interest.

The terms "wire" and "wire segments" are used for convenience and description, and in like manner will be understood to include any filar reinforcement element commonly used in engineered products such as tires, hose, or belts, and will be understood to include organic filar materials such as aramid, polyesters, rayon, nylon, and the like, and inorganic materials such as steel, and glass filaments, as to which the measurement of interface adhesion with rubber is of interest.

Figure 1:
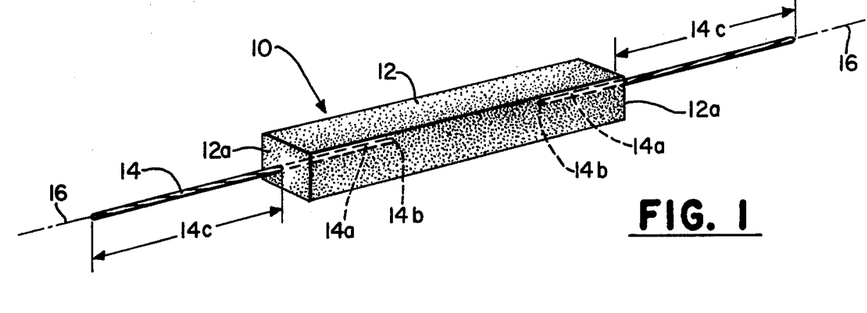
FIG. 1 is a view in perspective of a specimen in accordance wih the invention.

To carry out the test of interfacial adhesion, the invention provides for a test specimen 10 which is represented in FIG. 1. The specimen comprises a body 12 of rubber and a pair of wire segments 14 which are disposed along a line coincident with the centroidal axis 16 of the body. The body is preferably a square prism (geometric) elongated in the direction of the line in which the wire segments lie. Each segment 14 has a portion 14a embedded in the body such that the proximate ends 14b of the segments are spaced apart in the body 12 a predetermined minimum distance and such that a free length 14c, the remaining length of the wire segment extends perpendicularly from each of the square end faces 12a of the body. Preferably, the minimum distance from the wire axis to the boundary of the body 12 is at least three wire diameters in any plane normal to the axis line 16.

Figure 2:
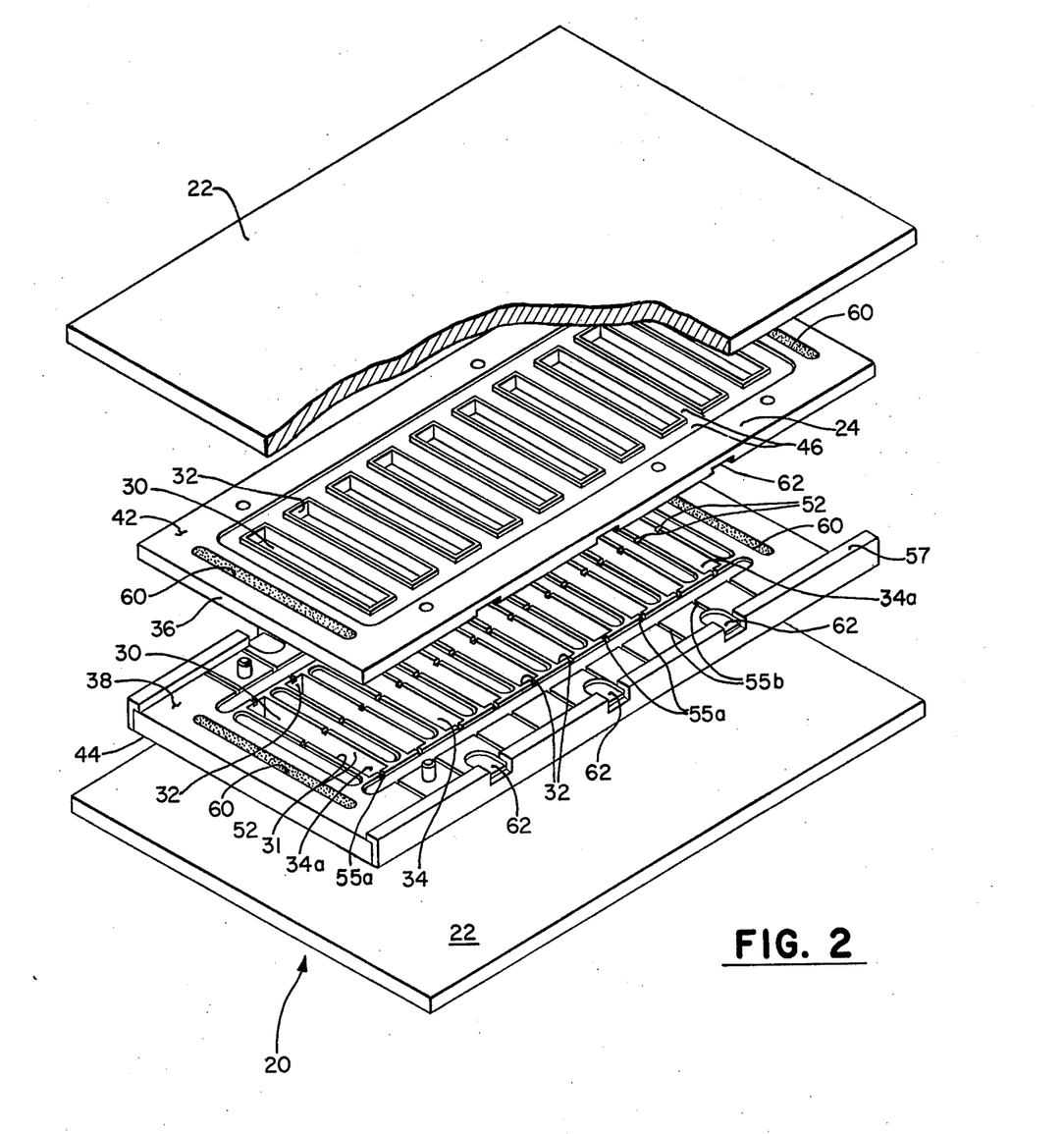
FIG. 2 is an expanded perspective view of a mold in accordance with the invention.
Figure 7:
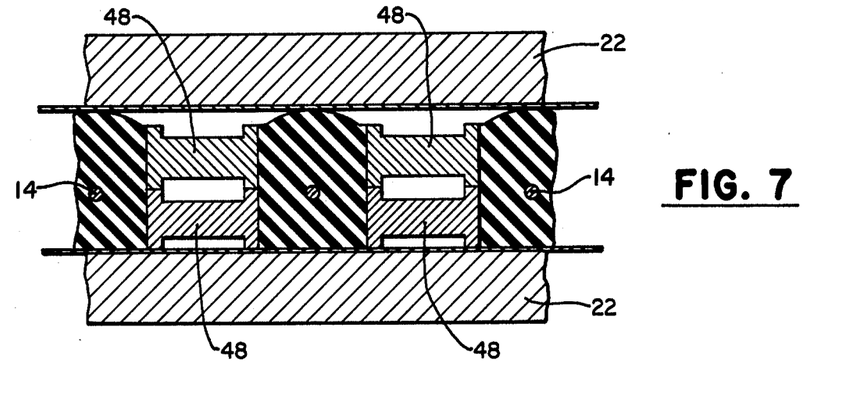
FIG. 7 is a view in expanded cross-section of a portion of the mold of FIG. 2.

The specimen 10 is formed and can be cured in a mold in accordance with the invention. Such a mold 20 is illustrated in FIG. 2 and comprises a pair of press plates 22 each with plane opposed parallel surfaces, an upper 24 and a lower 26 mating cavity plate each of which has a plurality of rectangular openings or pockets 30 formed by pairs of side 31 and end 32 walls. The cavity plates 24, 26 cooperate in mating juxtaposed position such that the respective side walls 31 and end walls 32 of the associated pockets form the respective side and end walls of a chamber 34 (refer also to FIG. 7) which form side and end walls of the body 12 of the specimen, the top and bottom surfaces of the body of the specimen being formed by the press plates 22. The upper and lower mold plates each have a plane first surface 36,38 which surfaces engage in mutual coplanar contact. Each has a second plane surface 42,44 for coplanar contact with the respectively associated plane press plate 22. A gutter 46 sunk in each surface 36,38; 42,44 of each mold plate provides means for accommodating excess, or flash, escaping from the respective pockets 30 as the specimen body 12 is compressed. In each mold plate a web 48, formed by sinking the respective gutters, remains and provides lateral support for the pocket side and end walls. The gutters in each mold plate define the thickness of the respective side and end walls of the pockets as well as the width of a narrow sealing land, coplanar with each of the respective surfaces, 36,38; 42,44 around the perimeter of each pocket 30. Each chamber 34 is provided with vent means to control the flow of rubber in and from the chamber. The vent means is provided in the lower mold cavity plate 26 by a pair of ports 52 open from the chamber to the adjacent gutter and which are cut through each side wall symmetrically with respect to the length between the end walls 32 of the chamber and at least approximately symmetrically between the surfaces 42,44 of the mold plates when the two plates are in mutual contact.

Means for positioning the two wire segments precisely along a common straight line which will coincide with the axis 16 of the specimen 10 comprises a plurality of grooves formed in the surface 38 of the plate 26. Two pairs of wire segment positioning grooves 55 extend collinearly, parallel to and equidistant from the side walls 31 of each pocket 30 in the plate 26.

The first pair of grooves 55a open between the pocket 30 and the adjacent gutter 46. A second pair of grooves 55b are aligned with the respective grooves of the first pair and are formed in the surface 38 between the gutter 46 and an abutment which provides means for fixing the axial location of the respective wire segments 14. The abutment means is provided gy a spline 57 which is affixed, one along each longitudinal edge of the lower mold plate 26, perpendicular to each side wall 31 and upward from the mating surface 38 such that a wire segment disposed in any such groove 55 abuts the spline 57 so as to locate the wire segments suitably within the body 12 of the specimen to be formed. But for the gutters, the grooves could extend from the pocket to the abutment spline.

Each cavity plate 24,26 is also provided with means for equalizing the cure of the specimens formed in the endmost chambers 34a with the cure attained in the remaining chambers 34. The equalizing means is provided simply by a slot 60 extending parallel to and spaced outward from the respective endmost pockets which form the chambers 34a. Each slot is located immediately outward of the adjacent gutter 46 and extends in length beyond the ends of the respective pockets, as well as through the respective cavity plates so as to block heat flow laterally toward the respective outer end of the plate. Each slot is filled with an insulating material having heat transfer properties about equal to the heat transfer properties of the rubber of the specimen. Most conveniently the material in the slot can be the same rubber as the rubber to be tested but when formed to fill the slots 60, can remain in place during use of the mold. The specimens cured in the endmost chambers are then equally useful with those cured in the remaining chambers.

Each mold plate is provided with a plurality of notches 62 which serve to accommodate a screwdriver or similar tool used to separate the upper and lower mold plates.

According to the invention, the specimen 10 is prepared by preforming a pair of coupons so that their respective fresh surfaces can be joined to embed the end portions of the respective wire segments.

The term "coupon" is used and will be understood to designate the respective constituent uncured rubber preforms two of which are joined to form the body 12 of the specimen 10.

Figure 3:
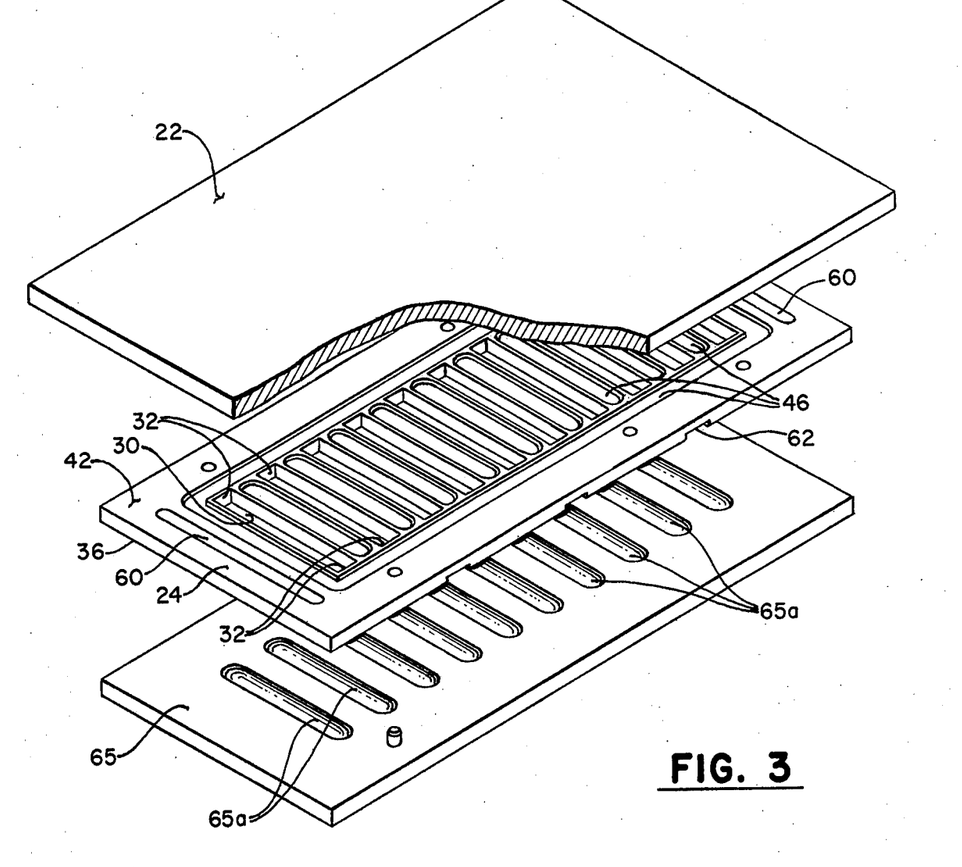
FIGS. 3 and 4 are expanded perspective views, respectively, of an upper half mold and a lower half mold used in the preforming stage of the specimen of FIG. 1.
Figure 4:
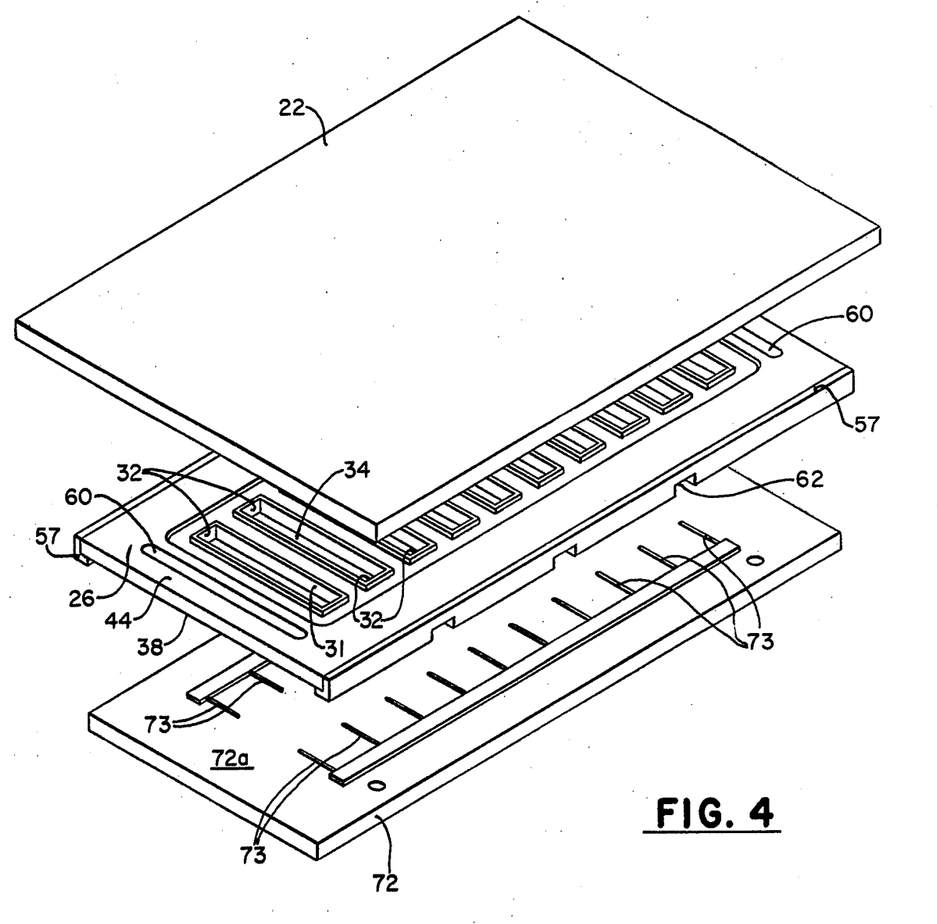

To provide means for preforming the respective coupons the invention provides a first preforming mold illustrated in FIG. 3 for the upper coupon and a second preforming mold illustrated in FIG. 4 for preforming the bottom coupon. Conveniently, the preforming mold in each case makes use of the upper 24 and lower 26 mold plates, respectively, each together with one of the plane press plates 22. Suitable dowel means are provided to align the upper and lower mold plates, located to prevent improper assembly.

Figure 5:
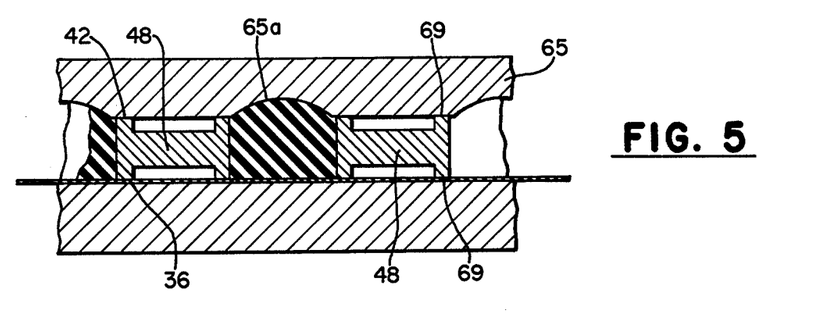
FIGS. 5 and 6 are views in enlarged transverse section of portions respectively of the molds of FIGS. 3 and 4.

Referring now to FIGS. 3 and 5, to provide a predetermined excess of rubber thereby insuring that the body of the specimen will be completely formed and suitably compressed, a bun plate 65 is provided with elongated concavities 65a, each of which is arcuate in cross-section normal to the axis and elongated, FIG. 3, to extend generally the length and width of the corresponding pockets 30 of the upper mold plate 24. The volume excess provided in the upper coupon by the concavity is determined such that the body of the specimen to be formed later will fill the chamber 34 in the mold of FIG. 2 and compressed sufficiently to achieve the desired cure and curing pressure of the particular rubber to be tested. In FIG. 5, the flash-receiving gutters 46 may be seen more clearly and particularly in that the location of each of the flash gutters with respect to the associated wall 31,32 of the pocket defines the thickness of such wall and a sealing land 69 approximately 16 millimeters in width surrounding each of the pockets 30.

Figure 6:
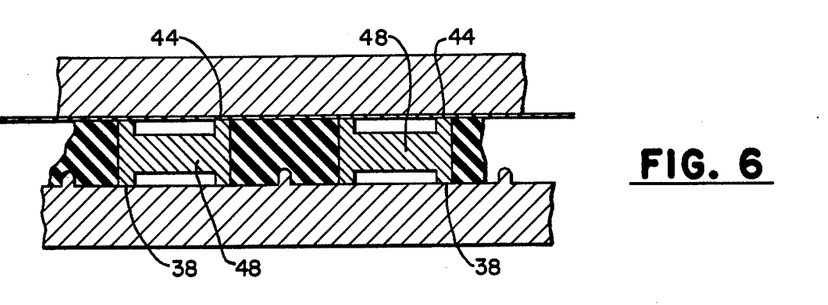

The preforming mold for the other of the two coupons is in like manner illustrated in FIG. 6 and comprises the previously described lower mold cavity plate 26, the other of the two press plates 22 or equivalent, and a groove-impressing plate 72 which provides wire segment seating recesses in the lower coupon in which recesses the respective wire segments 14 are seated. These recesses enable the wire segments to be placed and retained in line with the centroidal axis of the body and, particularly important with respect to the invention, such that their relative proximate ends are disposed not less than about 12 millimeters apart. This separation between the ends 14b of the wire segments has been found to be significant in the conduct of the test according to the invention and should not be less than the cross-sectional width of the body 12 normal to the axis 16. The groove-impressing plate 72 which provides means for forming the recesses has a plane surface 72a for coplanar contact with the first surface or mating surface 38 of the lower mold plate 26 and is provided with a plurality of pairs of ridges 73 on that surface, each of said ridges being coaxial with a longitudinal axis of a corresponding chamber 34 or pocket 30 such that the ridges 73 of the groove-impression plate occupy the respectively associated grooves of the lower mold plate during the preforming of the coupon. The respective gutter and the relation thereof to the respectively associated walls of the pocket are formed in the same manner and for the same purpose as described with respect to the upper mold plate. Between the surfaces 36 and 44 of of the mold plates and the respective press plates 22 there may be disposed a sheet of aluminum foil as shown in FIGS. 5 and 6.

The mold plates 24 and 26 are preferably, although optimally, nitrided to enhance their stiffness and surface hardness. The plates 24 and 26, as well as the base plate 65 and groove improving plate 72 are preferably treated with a coating of a polytetrafluoroethylene known as Teflon (registered trademark) on each of the surfaces exposed to contact with the rubber.

Upon completion of the preforming step, the bun plate 65 and the groove plate 72 are removed from the respectively associated mold plates. The lower mold plate 26 with coupons therein is placed on one of the plates 22. Wire segments which have been cut to predetermined lengths are then carefully disposed in the grooves 55 and in the recesses formed by the ridges 73 in the coupons retained in the pockets 30 and with outermost ends of the wire segments disposed to abut the splines 57 thereby locating their proximate ends 14b at the aforesaid minimum distance apart and in line along the axis 16. The upper mold plate 24 then with the upper coupons retained undisturbed in the respective pockets is superimposed on the lower mold plate 26 in the manner illustrated in FIG. 7. As mentioned earlier, aluminum foil as shown in FIG. 7 may be used or the press plates 22 be treated with Teflon (registered trademark). The press plate is then placed on the upper mold plate and in contact with the preformed coupon. The superimposed mold plates and press plates are then put under pressure load as in a conventional plate press. Under the load in the press, it will be seen that the upper press plate acts to move the press plate toward the lower press plate. This movement both compacts the respective coupons to form unitary bodies in each chamber with the respective wire segments embedded as described and extrudes excess rubber particularly from the ports 52. The vent ports through which the flash exits are sized so as to limit and control the exit of rubber from the chamber and thereby to assure a desired pressure in the rubber, and to insure that the movement of the rubber in the chamber is symmetric with respect to the wire axis thereby minimizing the displacement of the wire. It is desirable that the two wire segments be placed in and remain in coaxial alignment.

To prepare wire for test, wire is taken from certified creel spools, with precautions effective to avoid contamination of the wire being stored under nitrogen atmosphere in dessicated containers, handled with lint-free nylon gloves. The wire is cut to the desired length to provide the described wire segments which in the present embodiment 54.5 millimeters long. The wire may be cut with a standard shear cutter taking care that the wire is held perpendicular to the cutting edges of the shear and with precautions to prevent flaring of the wire ends. The wire may be coated or uncoated in accordance with conventional practice for wire used in engineered rubber products.

The preparation of rubber stocks for the test is accomplished on a conventional mill from which the rubber is sheeted to 7.6 to 7.8 millimeter thickness. The sheeted stock is placed between protective films to prevent contamination. Sheet stock of about 180 × 380 millimeters are cut and air trapped between film and rubber sheet is removed as with a roller to prevent bloom, contamination, loss of building tack, as well as to keep the surfaces dry. Suitable precautions are taken to maintain the quality of the rubber stock between the preparation thereof on the mill and a cutting out of individual strips.

The desired number of strips are clicked out to dimensions of 12 × 7.8 × 75 millimeters preferably in a multi-cavity clicking die. The strips so prepared are stored at room temperature in paper and polyethylene bags until needed but not for more than 48 hours. Then the protective film is removed from the clicked rubber strip and the strips are placed in the preform mold pockets 30 to form the coupons previously referred to, preferably with the aid of a Teflon (registered trademark) coated spatula or other nonabrasive utensil if needed. Care is taken not to contaminate the wire embedment surface. Aluminum foil, if used, is then placed over the exposed rubber strips in the respective preform mold plates 24, 26, and the press plate positioned over the foil, the arrangements being as illustrated in FIGS. 5 and 6. Next, each preform mold is placed between platens (not shown) in a curing press. It is convenient to press the two preform molds at one time in the same press.

In the preforming step the rubber strips are preformed for 1 minute at 135° C. Preform temperatures as low as 93° C. can be used if convenient. Preform temperatures higher than 155° C. are not recommended and the time and temperature schedule is herein regarded as cold forming. In the press the preform mold assembly resides for about 0.25 minutes at about 1500 pounds ram pressure. The ram pressure is then increased slowly to 15 tons over a period of about 0.5 minutes. In presses in which the pressure is attained in shorter times, it is advantageous to apply and release or "bump" the pressure two or three times.

Next, the preform molds are cooled. This may be accomplished in a water-cooled press to room temperature while under some 5 tons ram pressure. The time required is about 4 minutes. Alternatively, the preform molds can be cooled to room temperature by open air cooling and a common fan may be used if desired. Neither the preform molds nor the elements should be cooled in contact with water. Alternatively, if Teflon-plated press plates are used in place of aluminum foil, the cooling of the preform plates can be disregarded, although cooling is preferred.

Then the groover plate 72 of the lower preform mold is carefully loosened from the mold cavity plate 26. Flash is cut from each body 12 and removed from the flash gutters 46 as well as at the wire slots or grooves 55 if necessary.

The previously prepared wire segments 14, whether coated or uncoated, are inserted into the recesses which have been formed in the bottom coupons by the groover ridges 73, the segments being positioned in the straight line array in the respective grooves 55. One end of each wire segment is abutted against the spline 57. This serves to locate the embedded end 14b of each of the segments in the respective specimen bodies 12 as well as to prevent the wire from being forced axially outward of the body during the molding compression.

The bun plate 65 is then carefully loosened on both sides and removed from the mold plate 24. The aluminum foil if used is carefully removed and the flash is carefully cut from the bodies 12 and removed from the flash gutters 46. In removing flash it is advisable to use a non-abrasive tool. Alternatively, if the Teflon-coated press plate is used, the flash in the gutters is removed warm with the Teflon-coated spatula or other non-abrasive utensil.

The upper mold cavity plate 24 is then removed from the press plate and immediately mated to the bottom mold cavity plate 26 which has the wire segments positioned therein. The mentioned dowel pins serve to register the upper and lower mold cavity plates one with the other.

Aluminum foil, if used, is placed over the upper mold cavity plate 24 in contact with the buns formed in the concavities 65a and a press plate 22 is placed over the aluminum foil and the assembly 22,24,26,22 disposed in a curing press at 135° C. and pressurized to 15 tons on the ram while bumping at 2, 6, and 10 tons. In the case of instantaneous press pressure, the press is bumped twice. The specimens are cured for a time temperature and pressure suitable to the particular rubber of the specimen, the ram pressure being held at not less than 15 tons. The mold assembly may be cooled as previously discussed herein.

The aluminum foil, if used, is removed and the upper and lower mold cavity plates are separated as by use of a screwdriver or the like in the slots 62 after which the specimens are loosened and removed.

The interface adhesion of wire to rubber in accordance with the present invention is measured by the preparation and use of a specimen in which the respectively adjacent ends of two wire segments are embedded within the body of the particular rubber to be tested, the wire ends being isolated from each other and from the specimen exterior surface. In the specimen according to the present invention failure is initiated at one of the embedded wire ends such as occurs in testing to destruction a tire, at the belt edge, or at the clipper ends or at the ply ends.

It should also be noted that given the dimensions of the strip as cut from the rubber stock, the coupon formed in the upper preform mold is reduced from the volume of the original strip by approximately 29 percent. The coupon formed in the lower preform mold is decreased in volume approximately 21 percent. This reduction in volume first of all insures that the respective preform molds will be completely filled and suitably compressed. It has the additional advantage in that great precision in the preparation of the rubber stock as to thickness and as to cutting of the strip therefrom to prescribed dimensions is not required.

When the respective upper and lower coupons are united to form the body of the specimen in the curing mold, the volume is again reduced by approximately 5 percent. This reduction again insures that the mold will be entirely filled and the specimen body suitably compressed.

The respective ports 52 which are let into the two sidewalls 31 of each respective pocket 30 in the lower cavity mold plate 26 are 0.094 inches (about 2.4 mm) in width and 0.062 inches (about 1.6 mm) in depth.

The respective grooves 55a communicating between the pockets of the lower mold plate 26 and the adjacent flash gutters 46 are dimensioned suitably to accommodate the diameter of the wire segments which are to be placed therein. The end walls through which the respective grooves extend are typically about 1/16 inch (1.6 mm). When the curing mold is compressed, excess rubber of the body 12 to be cured is permitted to escape by way of the symmetrically located vent ports 52 thereby preventing the compression of the rubber from forcing the respective wire segments axially outwardly of the body. The short length (1.6 mm) of each groove due to the thickness dimension of the end walls permits such rubber as may be extruded around the wire to expand and form a bulbous collar around the wire immediately outward from the wall. We have discovered that the arrangement shown and described renders the specimen 10 less subject to variation in the test results than the arrangements of the prior art because the length of the flash along and surrounding the wire in the present embodiment tends to be more uniform. The presence of the bulbous collar renders what flash does occur more readily removed if such removal is desired. The size and symmetrical location of the ports 52 with respect to the end walls 32 and the axis 16 ensures that the rubber being compressed to form the body tends to flow both toward the wire groove 55a and toward the ports 52. This controls the flow in such a manner that the disturbance of the location of the wire segments with respect to the axis is minimized or eliminated. This is in contrast to the commonly experienced "floating" of the through wires in the samples prepared in accordance with the prior art procedures for testing adhesion.

Measurement of the maximum load exerted to pull a wire segment from the body of the specimen is in accordance with conventional operation of the testing machine. The respective free ends of this specimen are gripped in the machine, one in the fixed and the other in the movable jaw of the test machine. One of the jaws is then moved at a predetermined rate of 2 inches per minute (or 5 cm. per minute if the test machine is calibrated in metric units) away from the other while the force exerted on the specimen is indicated or recorded on a conventional strip chart.

In carrying out the adhesion test in a conventional tensile testing machine such as an Instron, the crosshead speed is preset at, for example, 2 inches per minute or if calibrated in metric units, at 5 centimeters per minute. The chart speed travel of the recorder is set at 5 inches per minute or if in metric units 10 centimeters per minute. The crosshead travel should be adjusted for not less than one full length of the specimen, in the present example, at 4 inches or 10 centimeters. The free length portions 14c of the wire segments are then clamped close to the point of their emergence from the rubber body but not closer than one-half inch, about 12 millimeters. The body 12 has no restraint, support, or contact other than by the two wire segments 14.

Next, the crosshead motion is started and allowed to continue until one of the wire segments pulls out completely from the rubber body of the specimen. The primary test report is that of the maximum force exerted at or prior to the pull-out of the wire segment from the specimen body and is called the pull-out force. This is the maximum force recorded in the chart recorder and may of course be displayed or recorded by other means.

Contrary to the belief of persons skilled in the art of testing, the step of preforming in accordance with the invention has demonstrated advantages. The purposes of the preforming described are: to generate a fresh uncontaminated surface upon which the wire segments can be placed as well as to insure the cohesion of the two elements or coupons which form the body of the specimen; secondly, to fix the location of the wire segments preferably using the grooves preformed into the surface of the coupon; and, thirdly, to fix the rubber volume at the onset of cure, insuring uniform pressure and penetration of the rubber to the wire interstices.

These advantages are especially important in that they offer some forgiveness in the control over variations in milled sheet thickness and the length of time the rubber surface is exposed in contrast to prior art procedures. We have discovered that the preforming step contributes significantly to the reproducibility, sensitivity, and usefulness of the data produced from the tests. By way of confirmation, specimens were prepared without preforming and examined under x-ray for comparison with specimens prepared according to the invention. In those specimens in which the preforming step was omitted, the wire segments were found to be out of plane and curved with repect to the desired axis of the specimen. Pull-out force was then measured in each of the two sets of specimens after immersing the specimens in hot water for several days. With the preforming step according to the invention, the coefficient of variation was determined to be 6.51 percent whereas in the specimens without preforming, the coefficient of variation was determined to be 10.76 percent.

The test according to the present invention is conveniently referred to as TCAT, an acronym for Tire Cord Adhesion Test.

In a further study comparing the TCAT test with the prior art SBAT test the TCAT failure forces, TCAT pull-out forces, were about one-third of those of the SBAT and were more reproducible. Each SBAT force value is an average of 13 values as each molded test piece contains in the ASTM test contained 13 usable wire lengths extending through the rubber block. The TCAT specimen was prepared and the test conducted as hereinbefore described. Both tests were conducted at room temperature at pull-out rates of 0.0008 meters per second. In a further study, the rankings of the failure forces of the different rubbers for the TCAT and the SBAT at room temperature were different. The scatter of failure forces within a given SBAT block (the 13 wires referred to) was greater than that for the repeat TCAT tests of the same rubber.

The discriminating power of a test depends strongly on a coefficient of variation characteristic of the data obtained. As illustration, a loss in the data quality by the change in the coefficient of variation from 3 to 6 percent may seem inocuous but the number of specimens must be increased by a factor of 3 to be able to detect a mean diffference of at least 10 percent. In this test, for example, 3 data points with a coefficient of variation of 2 percent will detect difference between two sets of data at a 95 percent confidence level if their means differ by at least 7 percent, while for a coefficient of variation of 4 percent the means must vary at least by 13 percent. Similarly, two groups of data with a mean difference of 9 percent require only two measurements if the coefficient of variation is two percent, while they need roughly 6 measurements if the coefficient of variation is 4 percent. Since the coefficients of variation have been determined to be typically about 7 percent with respect to the SBAT test but typically about 3 percent with the TCAT test of the present invention, the advantages are still further apparent.

Specimens 10 of the type described in connection with FIG. 1, in which the rubber bodies 12 were molded of two transparent rubbers and in which the wire segments 14 were cut from commercially supplied tire reinforcement wire.

A sample was supported in an Instron testing machine between two crossed circular polarizers and was pulled at the rate of 0.02 millimeters per second. The successive dark fringes in the central region away from the wire ends and the corresponding fringe patterns at the lower half of the specimen were photographed until the sample failed by pull out of the wire segment of the bottom wire in this case. As the speciment was elongated, dark fringes of increasing order appeared and disappeared in the central region of the specimen away from the wire ends. Their order was noted on the Instron chart at the coresponding values of the applied load. The stretched width of the sample was obtained from the respective photographs.

As the tension was increased, a complex fringe pattern developed indicating highly non-uniform stress. At an intermediate force, a small cavity visible through the specimen formed at the wire end and started growing as the wire pulled out. Thus, the failure was initiated at the wire end. As the sample was further elongated successive fringes of increasing order and stress emanated from the tip of the cavity and moved toward the wire emergent end. In the wire embedment regions the stress was very non-uniform, the fringe order decreasing from a maximum value at the tip of the cavity to unity at the wire emergent surface at both the bottom and top of the specimen. When the specimen begins to fail, the force extension curve goes through an erratic flat region. At this point the higher order of fringes at the cavity tip became fuzzy and disappeared, indicating that the stress in this region was being relieved. This process progressed along the wire segment.

These photoelastic stress observations are in marked contrast to the photoelastic stress observations of samples prepared in accordance with the teachings of the prior art using a transparent elastomeric matrix. In the prior art, the wire of the sample extends completely through the matrix and in performing the test the matrix is held or restrained while the wire is pulled from it, in fact, through it. In the prior art test the photoelastic observations show fracture to be initiated at the exterior surface near the emergent point of the wire. We have observed further that in the tests of the prior art particularly of the test in accordance with the ASTM static block adhesion test, the pulled out wires have extensive rubber coverage.

Failure is viewed as a process with three stages, (1) initiation of the failure in the form of a crack, cavity, or fissure, as at a stress raising flaw, (2) slow and stable propagation of the crack, cavity or fissure, and (3) catastrophic growth of the crack, cavity, or fissure. The present test is contrasted to the conventional practice such as the standard block adhesion test (SBAT) in that the specimen of FIG. 1 permits a pure and fully controlled adhesion test because the stresses are applied to the rubber at the wire-rubber interface and nowhere else.

From theoretical considerations, the interfacial adhesion test in accordance with the invention enables the determination of a quantity considered to represent an irrecoverable energy dissipated in creating a unit area of failed surface within the body of the specimen which we call the energy of adhesive fracture. This quantity is the energy needed for detaching a unit of interfacial area and is the measure of intrinsic adhesion. Unlike modulus, which is a property of the rubber itself, this quantity reflects a state of the rubber-wire interface. In our specimen, according to the present invention, the fracture initiating stress concentration is present at the embedded wire segment end within the body of the specimen, a well controlled site isolated from exterior boundaries. In contrast, in the prior art tests the fracture initiation occurs at or near a poorly controlled site on the exterior surface.

Specimens prepared of rubber compounds and identical wire segments were pulled to failure and the modulus of the several rubbers, e.g. natural rubbers with high sulfur content, was measured using a precision indentation technique. The TCAT values which spanned a considerable range, clustered narrowly about a line intercepting the origin of a plot of pull-out force versus the square root of modulus, in accordance with theory. It is thus demonstrated that the present test serves to determine the intrinsic energy of adhesion given by theoretical analysis as pull-out force divided by the square root of rubber modulus. The failures were adhesive in the sense that the pulled out wire segments were clean or tarnished or had at most a very thin and spotty rubber trapped in the interstices between the filaments. In contrast, a similar study was made of the static block adhesion test sample. The pull-out forces scattered widely about a best fit line with an intercept at a high value of force. The static block adhesion test is very insensitive to compound differences and apparently does not permit a fracture energy to be calculated. Also, the failures were relatively cohesive in that the wires had an appreciably greater rubber coating retained thereon after pull-out.

The improvement of the test according to the present invention relative to that of the static block adhesion test is further demonstrated by regression analysis. In all cases involving nine similar rubber compounds, the regression of the tire cord adhesion test (TCAT) pull-out forces on the square root of the modulus involved in 99.99 percent confidence of the slope. The correlation coefficient is 0.955 so that virtually all variation in the pull-out force is explained by the regression on the square root of the modulus. The intercept was close to zero and had a confidence of only 25 percent, hence cannot be distinguished from 0. From theoretical considerations, the conclusion is compelling that the TCAT test serves to determine intrinsic adhesion and that the similar materials tested have the same intrinsic adhesion to the wire used.

For the static block adhesion test (SBAT) the confidence was marginal (near 80 percent) on the slope of the regression line of the pull-out force on the square root of the modulus. The correlation coefficient is 0.155 so the regression on the square root of the modulus accounts for but a small part of the variation in the pull-out force. The intercept was quite high, approximately 1000 Newtons and since it had a confidence of 99.9 percent, the true SBAT intecept almost certainly is not zero. This intercept is an extraneous modulus effect associated with the pinching action in the SBAT slot opening; it is meaningless since the finite force at a vanishing modulus implies infinite strain energy. Clearly, the effect of modulus is not well defined, and SBAT cannot be viewed as distinguishing the effect of modulus from that of intrinsic adhesion.

Alternately, the TCAT mold may be modified to accommodate long wire or cord filaments by removal of the abutment spline. In this case, a rubber gasket is fitted into the flash gutter over the filaments as they pass through it to prevent outward movement/displacement of the filament during cure. Specimens of this type construction may be tested on the Instron or other testers with the conventional cord type grips.

While certain representative embodiments and details have been shown for the purpose of illustrating the invention, it will be apparent to those skilled in the art that various changes and modifications may be made therein without departing from the spirit or scope of the invention.

What is claimed is:

1. Method for testing interface adhesion of wire and rubber comprising the steps of:
    (a) cutting a plurality of segments each of predetermined length of such wire;
    (b) preparing said rubber in sheet form of predetermined thickness in its uncured state and cutting from such sheet a plurality of coupons of predetermined length and width;
    (c) preforming said coupons each in preforming means to form a plurality of pairs of uncured preformed coupons;
    (d) placing said wire segments in surface contact one pair respectively with a first coupon of each pair thereof such that each segment of said one pair thereof be located in a single straight line, such that a portion of each segment be seated on said first coupon and the remaining portion thereof be extended outward lengthwise of said coupon such that the proximate ends of each said segments of such pair be spaced apart a predetermined minimum distance along such line;
    (e) disposing the other coupon of each pair thereof and a respectively associated first coupon in face-to-face contact with the respective pairs of wire segments each having a portion embedded therein so associated each pair of coupons to form an integral test specimen;
    (f) molding and curing the specimens in mold means comprising associated parts of said preforming means;
    (g) releasing said specimens from said mold means;
    (h) gripping only the wire segments of a selected specimen and pulling said wire segments oppositely along said single line at a predetermined rate while measuring the force exerted to separate one of said wire segments from such specimen;

(i) said force so measured being useful to determine the interface adhesion of said wire and said rubber.

2. A specimen mold for preforming a plurality of coupons each having a predetermined volume and subsequently for uniting respectively associated pairs of said coupons, each pair with a pair of wire segments respectively disposed and spaced apart along a single line, the mold comprising:

(a) a pair of press plates each having opposed parallel plane surfaces;

(b) first and second mating cavity plates each having spaced opposed parallel plane mating surfaces and having means defining a plurality of rectangular preform pockets open between said mating surfaces;

(c) a bun plate having a plurality of concavities each aligned cooperatively with an associated one of said pockets of said first cavity plate and cooperable with the first of said press plates to form a closed cavity for pre-forming a first coupon of an uncured rubber;

(d) a groover plate having a plane surface and a plurality of parallel ridges on said surface each aligned cooperatively with an associated one of said pockets of said second cavity plate and cooperable with the other of said press plates to preform a second coupon of said uncured rubber having therein a pair of grooves in straight line array, the proximate ends of said grooves being spaced apart a predetermined minimum distance and each said groove being adapted to seat a portion of a wire segment therein;

(e) said mating cavity plates being cooperable in mating juxtaposed position to register respective pockets thereof in matched relation and cooperable with said press plates to define molding and curing chambers each for uniting a first and a second coupon and a pair of said wire segments to form said test specimen having predetermined length portions of said wire segments embedded therein and remaining portions extending therefrom along said line.

3. A specimen mold as claimed in claim 2, flash accommodating gutter means extending around the perimeter of each said pocket, each said pocket having side walls and end walls, means defining a narrow land coplanar with the mating surface surrounding each pocket and vent means for controlling flow of uncured rubber in and from each said chamber, the vent means comprising a pair of ports extending between said chamber and said gutter means each being located at the middle of the length of the associated side wall.

4. A specimen molding apparatus as claimed in claim 2 comprising:

(a) means for equalizing cure in the endmost pockets with cure in the remainder thereof, comprising:

(I) an elongated slot spaced outwardly from and parallel to full length of each of the endmost ones of said plurality of mold pockets, and open to said surfaces, each said slot being filled with an insulating material having heat transfer properties about equal to like properties of the material molded and cured in said mold plate, whereby in the endmost ones of said mold pockets the material molded and cured receives cure temperatures like that in the mold pockets between said endmost ones.

5. A method of testing interface adhesion of wire and rubber comprising:

(a) preparing a pair of wire segments of predetermined length;

(b) forming an elongated body and arranging said segments along a centroidal axis of said body with their adjacent ends within said body and spaced a predetermined minimum distance apart along said axis;

(c) wherein the minimum dimension of said body in any plane normal to said line is sufficient to render negligible any interaction between the adhesion of the wirecompound interface and the exterior of said body;

(d) pulling said segments oppositely along said axis at a controlled rate while maintaining said body free of external restraint; and (e) measuring the force exerted in pulling at least one of said segments from said body, the force so measured, being useful to determine the value of said interface adhesion.

6. A method of testing interface adhesion of wire and rubber comprising:

(a) preparing two wire segments each of predetermined length;

(b) preforming two coupons of uncured rubber to provide for each a fresh, uncontaminated face and a predetermined volume;

(c) placing said wire segments, each with a length portion thereof in seated contact with said fresh face of one of said preformed coupons and the remaining length portion thereof extending freely outward lengthwise of each coupon along a single straight line and with the proximate ends of the segments spaced apart along said line, then placing said fresh face of the other of said coupons in face-to-face contact with the fresh face of said one thereof and thereby embedding the first said length of each said segment and forming a unitary body of the pair of coupons with the proximate ends of two wire segments embedded in and spaced apart in such body a predetermined minimum distance;

(d) pulling said wire segments apart at a predetermined rate while maintaining said body free of restraint;

(e) measuring the force required in said pulling said force being useful to determine interface adhesion of said wire and rubber.

7. Apparatus for preparing a test specimen comprising:

(a) a pair of press plates each having plane parallel surfaces;

(b) an upper mold plate and a lower mold plate each having a plane first surface for mutual coplanar mating contact with the other mold plate and a second plane surface parallel to and spaced from said first surface, each said mold plate having a plurality of means defining a molding pocket each comprising a pair of side walls and a pair of end walls perpendicular to said first surface, each said pocket means cooperating, when the press plates and mold plates are in such mutual contact, to define a chamber having an axis parallel to and equidistant from said sidewalls and from each said second plane surface;

(c) flash accommodating gutter means for receiving excess rubber from the chambers and comprising a plurality of gutters each determining the thickness of at least one of said side walls;

(d) each said chamber having wire seating means for positioning a pair of wire segments collinearly of said axis and spaced axially apart a predetermined minimum distance, said wire seating means comprising a pair of collinear grooves open to said first surface of said lower mold plate and through a respectively associated end wall from said chamber to the adjacent gutter and a further pair of grooves respectively aligned with the grooves of the first-mentioned grooves extending in said first surface axially outward from the gutter associated with the respective end wall;

(e) each said chamber having vent means for controlling flow of rubber in and from the chamber and comprising a pair of ports opening from the chamber to the respectively adjacent gutters, said ports being located symmetrically with respect to said axis and said end walls;

(f) abutment means for fixing axial location of said wire segments and including a spline affixed one on each longitudinal edge of the lower mold plate, extending perpendicular to each said axis and upward from said first surface such that a wire segment disposed in any such groove abuts said spline thereby to locate the end of such wire segment with respect to the other segment of said pair in said chamber.

8. Apparatus as claimed in claim 7 comprising:
(a) preforming means for cold preforming a pair of coupons each having a fresh surface, the latter surfaces to be joined to embed end portions of two collinear said wire segments therebetween;
(b) said preforming means including said upper and said lower mold plates;
(c) bun plate means having a plurality of concavities of predetermined volume each associated with a respective one of said pockets of said upper mold plate;
(d) one of said press plates, said bun plate and said upper mold plate therebetween being cooperable to define a plurality of closed pockets each defining the shape and volume of one of said coupons;
(e) groover plate means comprising a groove impressing plate having a plane surface cooperable with said first surface of said lower mold plate and a plurality of pairs of ridges on said plane surface each pair of said ridges being such that when the plane surface of the groove-impressing plate and the first surface of the lower mold plate are juxtaposed in coplanar contact, said ridges occupy the respectively associated grooves of the lower mold plate;
(f) the groover plate means, the second press plate and the lower mold plate disposed therebetween, being cooperable to define a plurality of closed pockets each defining the shape and volume of the other of said coupons, said shape including a pair of wire seating grooves extending inward from respectively associated end walls collinear with said axis and terminating at the proximate ends thereof a predetermined minimum axial distance apart;
(g) The volume of said chamber between second surfaces being at least sufficiently less than the combined volume of said pair of coupons to insure flow from said chamber to respectively adjacent gutters when said upper, said lower, and said press plates are superimposed under compressive load to join said fresh surfaces of said coupons with said pair of wire segments therebetween.

9. Apparatus for preparing a test specimen comprising:
(a) preforming means for cold preforming a pair of coupons each having a fresh surface, the fresh surfaces of the respective coupons to be joined to embed end portions of each of a pair of collinear wire segments therebetween;
(b) a pair of press plates each having plane parallel surfaces, an upper mold plate, and a lower mold plate, each having a plane first surface and a plane second surface parallel to and spaced therefrom, each mold plate having a plurality of wall means each comprising a pair of side walls and a pair of end walls, said pairs of side and end walls being perpendicular to said first surface thereof and defining respectively a plurality of pockets;
(c) bun plate means comprising a plate having a plane surface and a plurality of concavities of predetermined volume sunk in said surface each concavity associated with a respective one of said pockets of said upper mold plate;
(d) said bun plate means, one of said press plates and said upper mold plate therebetween cooperating to define a plurality of closed pockets each defining the shape and volume of one of said coupons;
(e) groover plate means comprising a groove impressing plate having a plane surface cooperable with said first surface of said lower mold plate and a plurality of ridges on said plane surface each pair of said ridges being coaxial with an axis extending longitudinally of the respectively associated pocket equidistant between the sidewalls thereof and a predetermined distance below the first surface of said lower mold plate, said ridges being such that when the plane surface of the groove impression plate and the first surface of said lower mold plate juxtaposed in coplanar contact, said ridges occupy the respectively associated grooves of the lower mold plate;
(f) said lower mold plate having wire positioning means for positioning a pair of wire segments disposed thereon in straight line array and spaced axially apart a predetermined minimum distance;
(g) said pockets of said lower mold plate each having an axis disposed longitudinally thereof parallel to and equidistant from respectively associated sidewalls and parallel to and spaced a predetermined distance below said first surface of said mold plate;
(h) said groover plate means, the other of said pair of press plates and said lower mold plate therebetween being cooperable to define a plurality of pockets each defining the shape and volume of the other of said coupons, said shape including a pair of wire seating grooves extending inward from the respectively associated end walls collinearly with said axis and terminating at proximate ends thereof a predetermined minimum axial distance apart;
(i) the volume of said chamber between said second surfaces being at least sufficiently less than the combined volume of said pair of coupons to insure flow from said chamber to respectively adjacent gutters when said upper, said lower, and said press plates are superimposed under compressing load to join said fresh surfaces of said coupons with said pair of wire segments therebetween.

10. A specimen molding apparatus for wire-to-rubber adhesion test comprising:
(a) means for preforming a pair of coupons of uncured rubber each having a fresh uncontaminated uncured surface and a predetermined volume;
(b) means for forming seating recesses for a pair of wire segments in straight line spaced apart array in one of said fresh surfaces;
(c) mold means for matingly juxtaposing said fresh surfaces with said wire segments therebetween to form the uncured specimen;
(d) means for compressing said uncured specimen while curing the same; and
(e) vent means for controlling flow of said rubber in and from said specimen during said curing.

* * * * *